(12) United States Patent
Chini

(10) Patent No.: US 11,141,188 B2
(45) Date of Patent: Oct. 12, 2021

(54) SAFETY SCALPEL

(71) Applicant: Andrea Chini, Rome (IT)

(72) Inventor: Andrea Chini, Rome (IT)

( * ) Notice: Subject to any disclaimer, the term of this patent is extended or adjusted under 35 U.S.C. 154(b) by 0 days.

(21) Appl. No.: 16/761,518

(22) PCT Filed: Nov. 7, 2018

(86) PCT No.: PCT/IT2018/000143
§ 371 (c)(1),
(2) Date: May 5, 2020

(87) PCT Pub. No.: WO2019/092760
PCT Pub. Date: May 16, 2019

(65) Prior Publication Data
US 2020/0261105 A1   Aug. 20, 2020

(30) Foreign Application Priority Data
Nov. 10, 2017   (IT) ...................... 102017000128663

(51) Int. Cl.
*A61B 17/3211*   (2006.01)

(52) U.S. Cl.
CPC . *A61B 17/3211* (2013.01); *A61B 2017/32113* (2013.01)

(58) Field of Classification Search
CPC .......... A61B 17/3209; A61B 17/32093; A61B 17/3211; A61B 2017/32113; A61B 5/1411; A61B 5/150053; A61B 5/150374; A61B 5/150381; A61B 5/150412; A61B 5/150442; A61B 5/150473; A61B 5/15048; A61B 5/150488; A61B 5/150496; A61B 5/150534
See application file for complete search history.

(56) References Cited

U.S. PATENT DOCUMENTS 3,294,089 A * 12/1966 Brookfield ............ A61M 5/343
                                                      604/241
3,688,407 A    9/1972 Paquette
5,571,127 A * 11/1996 DeCampli .......... A61B 17/3211
                                                       30/125
5,620,455 A    4/1997 Grigoletto
(Continued)

FOREIGN PATENT DOCUMENTS

WO        9627336 A1    9/1996
WO     2016197001 A1   12/2016

*Primary Examiner* — Ryan J. Severson
(74) *Attorney, Agent, or Firm* — David Guerra

(57) ABSTRACT

A safety scalpel has an elongated central body (1) having at each of its opposite ends (2, 3) a retractable lancet system comprising: a protection member (4) having a slot (12) and being connected to the elongated central body (1) and concentric thereto; a prismatic guide concentric to the elongated central body (1) and located inside the protection member (4); and a lancet holding member 20) consisting of a distal part (21) in the form of a prismatic member in which the lancet (24) is frontally inserted, and a proximal part (22) formed by two parallel arms (25, 26) having an end integral with the prismatic member, an arm (25) of them being slidable in contact with the prismatic guide, and the arm (26) carrying on a button (27) protruding from the slot (12) and provided with retaining elements (28) intended to be received into stop recesses (10, 11) of the slot (12).

6 Claims, 4 Drawing Sheets

(56) References Cited

U.S. PATENT DOCUMENTS

| | | | |
|---|---|---|---|
| 6,015,419 A | 1/2000 | Strome et al. | |
| 7,022,128 B2* | 4/2006 | Morawski | A61B 17/3211 |
| | | | 30/162 |
| 8,303,614 B2 | 11/2012 | Schraga | |
| 9,044,265 B2* | 6/2015 | Cote | A61B 17/3211 |
| 10,555,755 B2* | 2/2020 | Werner | A61B 17/3211 |
| 11,013,529 B2* | 5/2021 | Quinn-Gorham | |
| | | | A61B 17/3213 |
| 2009/0204136 A1* | 8/2009 | Endo | B26B 1/08 |
| | | | 606/167 |
| 2011/0098734 A1 | 4/2011 | Cote | |
| 2018/0125520 A1* | 5/2018 | Lehn, Jr. | B26B 1/08 |
| 2020/0261105 A1* | 8/2020 | Chini | A61B 17/3211 |

* cited by examiner

SAFETY SCALPEL

TECHNICAL FIELD

The present invention relates to a safety scalpel.

BACKGROUND ART

US2011/0098734 A1 discloses a retractable safety knife having a hollow handle with an opening at one end thereof, a pusher that is movably disposed within the handle and is operable by a user, and a blade connected to the end of the pusher. When the pusher moves from a blade-retracted position to a blade-extended position, the blade extends outwardly from the handle opening. The handle has a longitudinal slot where a button protrudes from the slot, the button being provided at least with a downward projection. The longitudinal slot has at least two lateral notches corresponding to the retracted and, respectively, extended position of the blade. The button latches into one or the other position depending on the desired position. US2011/0098734 A1 shows that knives with a movable blade are known with respect to the handle with the use of a single hand; its mobility allows the protection of the blade when it is not used. Only one blade can be chosen at a time.

U.S. Pat. No. 8,303,614 B2 discloses a lancet device, including an elongate central body having hollow ends; in each of them a needle holding element protected by a cap is pressed. U.S. Pat. No. 8,303,614 B2 proves that a device with two needles individually protected with a cap is known. The cap must be applied by using both hands.

SUMMARY OF THE INVENTION

The present invention aims to overcome the drawbacks of the prior art. An object of the present invention is to allow a choice between a pair of lancets, ensuring safety against accidental cuts that may occur when applying the protection cover of a lancet.

Another object of the invention is to make a surgery most efficient, making available to the surgeon two different but equally protected lancets.

Another object of the invention is to provide a safety scalpel with an ergonomic shape which facilitates its use.

To solve these and other objects, the invention provides a safety scalpel comprising an elongated central body having opposite ends for respective lancets,
wherein the elongated central body comprises a retractable lancet system connected at each of its opposite ends, wherein the retractable lancet system comprises:

a protection member having a slot with stop recesses, a distal opening and an opposite closed end that is connected to the elongated central body, and concentric thereto;

a prismatic guide concentric to the elongated central body that is located inside the protection member; and a lancet holding member consisting of:

a distal part in the form of a prismatic member in which a lancet is frontally inserted, and a proximal part formed by two parallel arms having an end integral with the prismatic member, a first arm of them being slidable in contact with the prismatic guide and a second arm carrying on a button protruding from the slot of the protection member and being provided with retaining elements intended to be received into the stop recesses of the slot.

Such a scalpel allows the surgeon to use either of the lancets in the same surgery, without any risk of injury in the passage of the scalpel between the surgeon and the scrub nurse, or while a lancet is being covered.

As the scalpel has two lancets being alternately used, its passage from the surgeon to the scrub nurse takes place only once rather than twice, as happens when using a scalpel having only one lancet.

The opening and closing of the protection member can be performed by using one hand.

Advantageously, the lancets may be different from one another in order to perform different functions.

Conveniently, the protection members are rotated 180 degrees with respect to each other around the axis of the elongated central body, so as to allow the change of lancet with its simple rotation, after the closure of the first protection member and after the opening of the second one.

Suitably, the protection members are shaped flared towards their front opening in an ergonomic form for gripping.

The opposed closed end of the protection members is connected to the elongated central body by a bayonet coupling, but, alternatively, another connecting means may be employed, for example screw or interlocking.

The accuracy and stability of the stop recesses is guaranteed by the elastic behavior of the arm carrying on the button of the lancet holding member.

BRIEF DESCRIPTION OF DRAWINGS

Further features and advantages of the present invention will become most clear from the indicative, and therefore non-limiting, description of a preferred but not exclusive embodiment of a safety scalpel, as illustrated in the accompanying drawings in which.

DESCRIPTION OF INVENTION EMBODIMENTS

Figure 1:
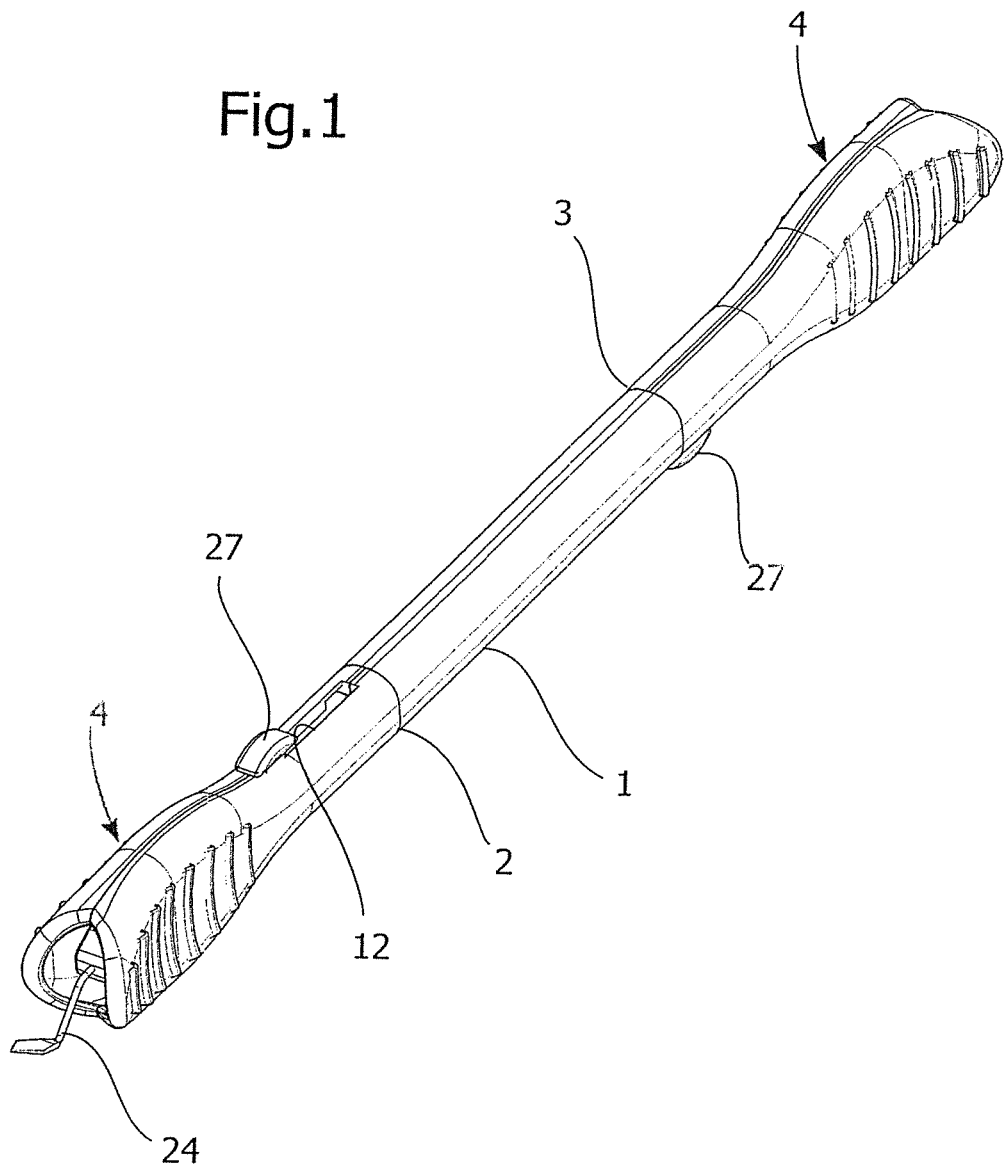
FIG. 1 is a perspective view of the safety scalpel according to the invention.

Reference is first made to FIG. 1, which is a perspective view of the safety scalpel according to the invention.

The safety scalpel comprises an elongated central body 1 having opposite ends 2, 3. Connected to each of the opposite ends 2, 3 is a retractable lancet system comprising a protection member 4. Although the protection members are two, they are indicated with the same reference numeral and only one of them is described, being identical.

Figure 2:
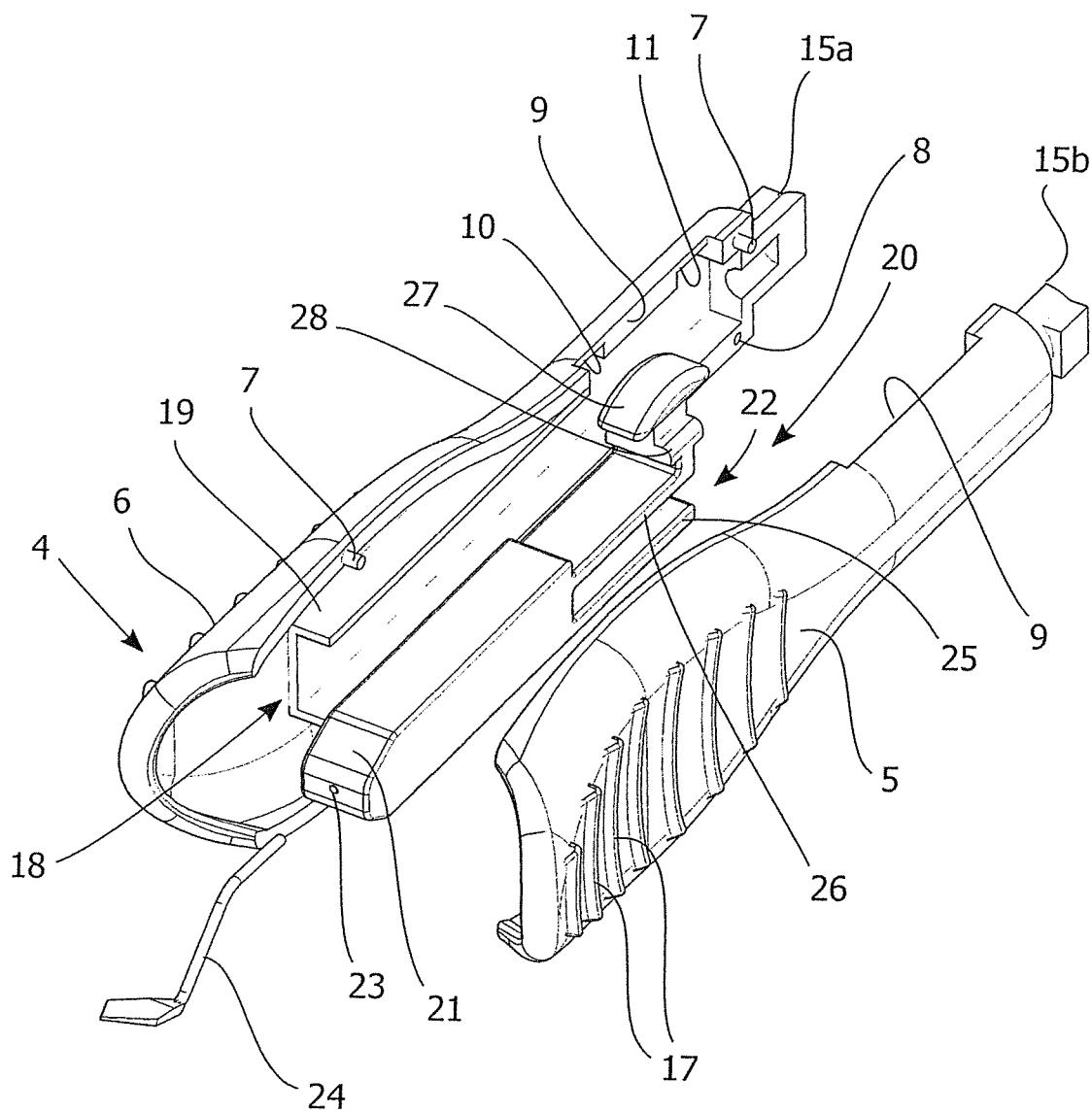
FIG. 2 is an enlarged exploded perspective view of the safety scalpel in FIG. 1, representing only one protection member extracted from the elongated central body.

Reference is made also to FIG. 2 which is an enlarged exploded perspective view of the safety scalpel in FIG. 1, representing only one protection member extracted from the elongated central body.

The protection member 4 is formed of two equal parts or cheeks 5, 6 which can be closed on one another by means of pins generally indicated with 7 and corresponding holes indicated with 8. Made on one side of each cheek 5, 6 is a depression 9 with stop recesses 10, 11 facing the inside of the protection member 4. The two depressions 9 form a slot 12, when the cheeks 5, 6 are mounted one on the other, as shown in FIG. 1.

Figure 3:
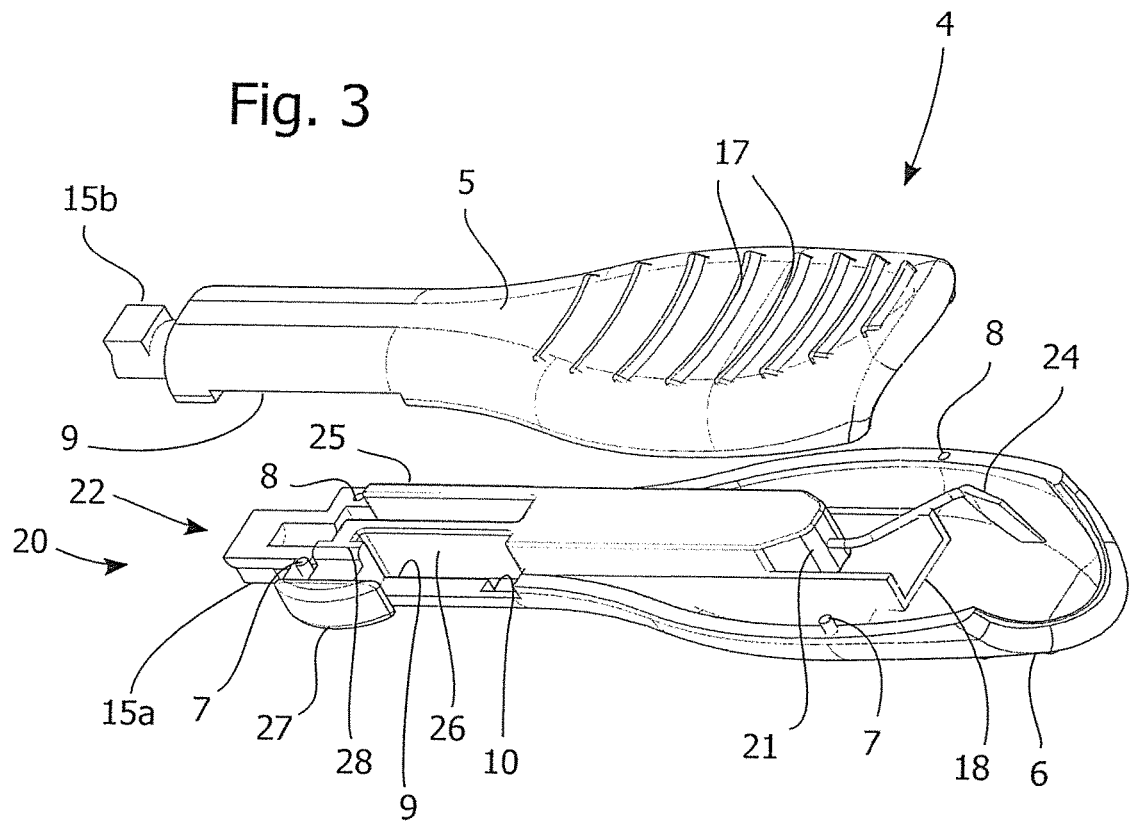
FIGS. 3 and 4 are partially exploded perspective views of the protection member of FIG. 2 with a lancet holding member in a retracted and, respectively, advanced position.
Figure 4:
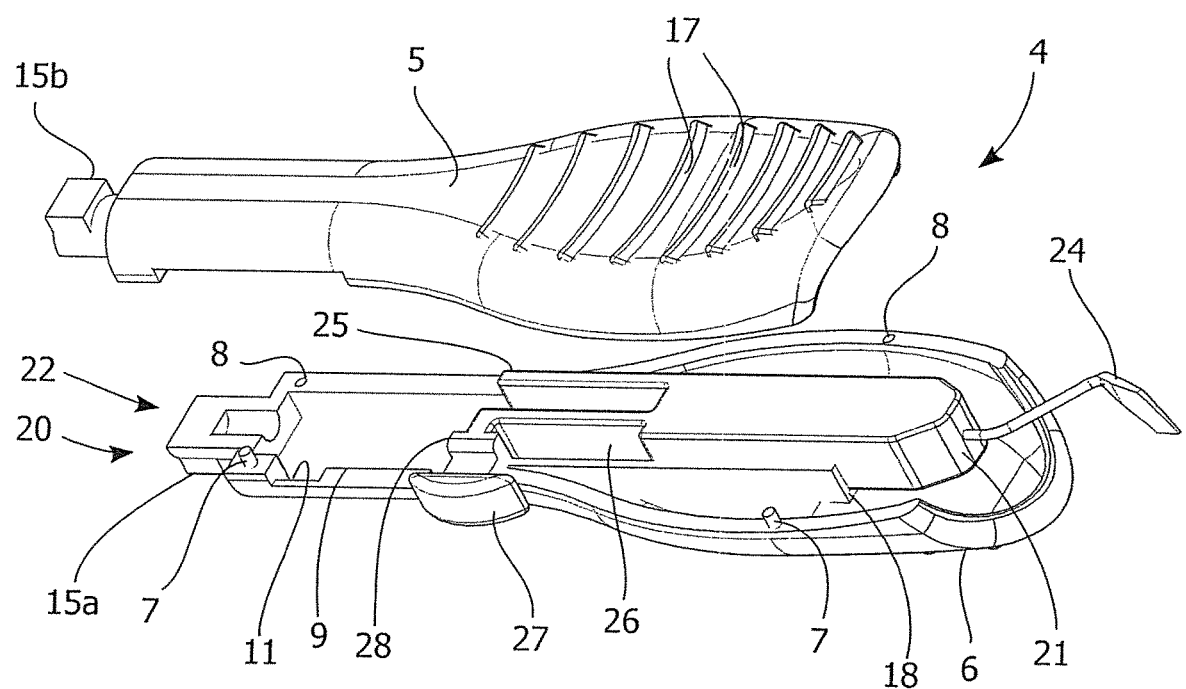
Figure 5:
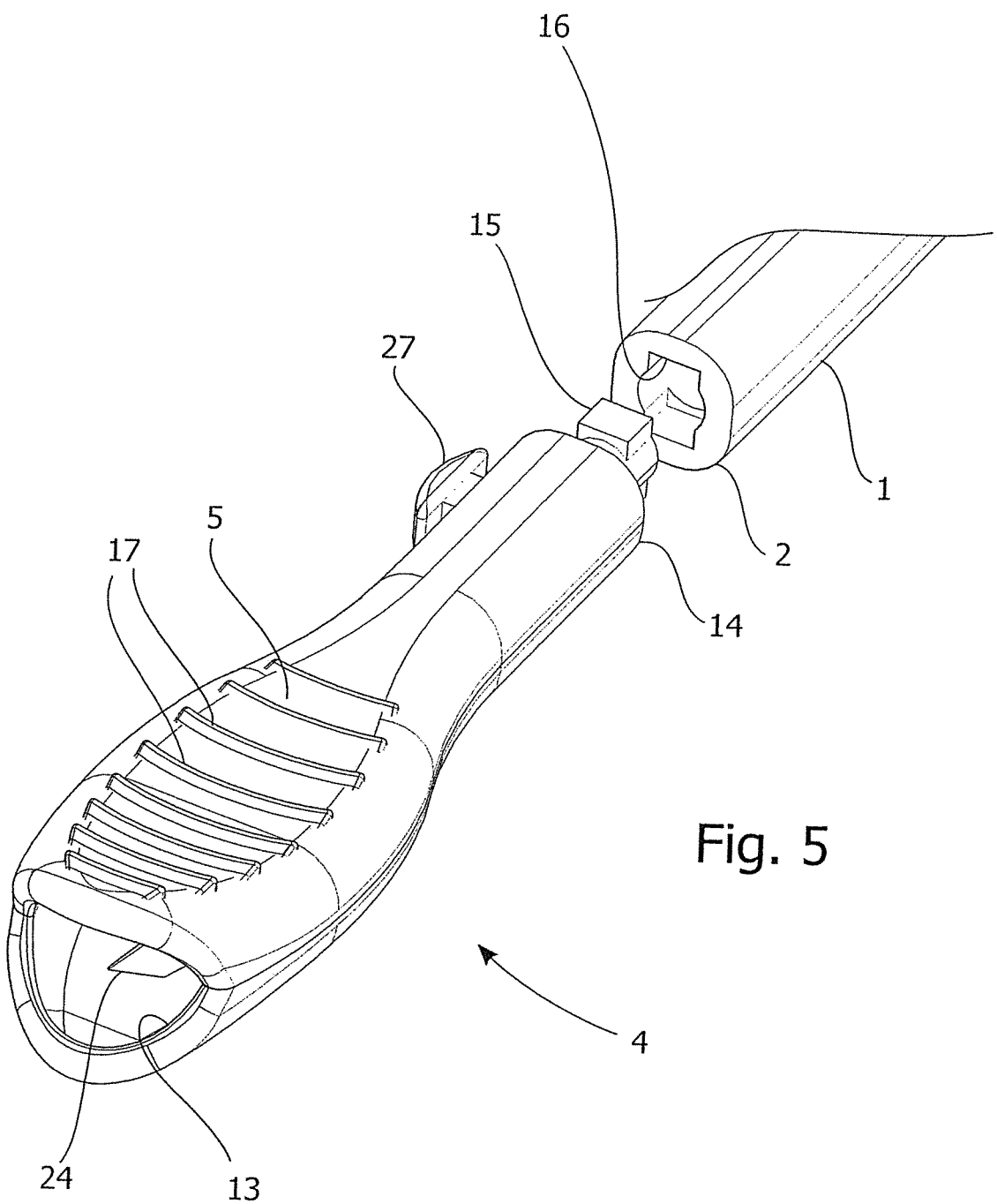
FIG. 5 is an assembled perspective view of the protection member in FIG. 2 and of a part of the elongated central body from which it is separated.

Referring to FIG. 5, which is an assembled perspective view of the protection member in FIG. 2 and of a part of the elongated central body from which it is separated, it is seen that, in the assembled arrangement, the protection member 4 has a front opening 13 and a closed opposite end 14 that is connected to the elongated central body 1 and is concentric thereto. The connection between the protection member 4 and the elongated central body 1 is made by a bayonet male coupling 15, which is inserted into a corresponding cavity 16 obtained in the elongated central body 1. Advantageously, also the bayonet male coupling 15 is formed by two halves 15*a* and 15*b*, as shown in FIGS. 3 and 4, which are partially exploded perspective views of the protection member in FIG. 2 with a lancet holding member in a retracted and, respectively, advanced position. The cheeks 5 and 6 have a flared shape towards their front opening 13 and are provided with external projections 17 useful for an ergonomic grip of the scalpel.

Inside each protection member 4 there is a prismatic guide concentric to the elongated central body 1. The prismatic guide is formed by two C-shaped elements 18 (FIG. 2), having a reduced wing 19 to form the slot 12 (FIG. 1) in correspondence with the depression 9 (FIGS. 2 to 4).

Mounted inside the prismatic guide is a lancet holding member 20 concentric to the elongated central body 1. The lancet holding member 20 is constituted by a distal part 21 and a proximal part 22 with respect to the elongated central body 1. The distal part 21 is a prismatic member provided with a hole 23 in which a lancet 24 is inserted. The proximal part 22 is formed by two parallel arms 25, 26. The arm 25 is sliding in contact with the prismatic guide, while the arm 26 carries on a button 27 protruding from the slot 12 of the protection member 4. The button 27 is provided inferiorly with retaining elements 28 intended to be received in the stop recesses 10, 11 of the slot 12. The arm 26 is elastic so as to be able to flex with respect to the prismatic member of the distal part 21.

In factory assembly, the lancet holding member 20 is inserted into a C-shaped element 18 of one of the cheeks 5 and 6, which are then closed one on the other. The protection members 4 are rotated 180 degrees relative to each other around the axis of the elongated central body 1, as shown in FIG. 1. This is done to facilitate, in use, the extraction and retraction of the lancet 24 in the relevant protection member, when changing from one lancet to the other with the simple 180 degrees rotation of the scalpel that is carried out with one hand.

In particular, the lancet 24 is extracted by sliding the button 27 from the proximal stop recess 11 to the distal stop recess 10, where it is held by means of its retaining elements 28.

It should be understood that the intended objects of the invention are achieved, in particular that of providing a safe scalpel in use, which may allow a choice between a pair of lancets and make surgical intervention most efficient. The ergonomic shape that facilitates its use should not be underestimated. Although a type of connection between the protection member and the elongate central body has been described in detail, it is to evident that this does not exclude that equivalent coupling means can be used.

The invention claimed is:

1. A safety scalpel comprising an elongated central body (1) having opposite ends (2, 3) for respective lancets (24),
   wherein the elongated central body (1) comprises a retractable lancet system connected at each of its opposite ends (2, 3),
   wherein the retractable lancet system comprises:
   a protection member (4) having a slot (12) with stop recesses (10, 11), a distal opening (13) and an opposite closed end (14) that is connected to the elongated central body (1), and concentric thereto;
   a prismatic guide concentric to the elongated central body (1) that is located inside the protection member (4); and
   a lancet holding member (20) consisting of:
   a distal part (21) in the form of a prismatic member in which the lancet (24) is frontally inserted, and
   a proximal part (22) formed by two parallel arms (25, 26) having an end integral with the prismatic member, a first arm (25) of them being slidable in contact with the prismatic guide and a second arm (26) carrying on a button (27) protruding from the slot (12) of the protection member (4) and being provided with retaining elements (28) intended to be received into the stop recesses (10, 11) of the slot (12).

2. The safety scalpel according to claim 1, wherein the protection members (4) are rotated 180 degrees with respect to each other about the axis of the elongated central body (1).

3. The safety scalpel according to claim 1, wherein the protection members (4) are flared toward their front opening (13) in an ergonomic shape for gripping.

4. The safety scalpel according to claim 3, wherein the protection members (4) are formed by two cheeks (5, 6) having external projections (17).

5. The safety scalpel according to claim 1, wherein the opposite closed end (14) of the protection members (4) is connected by a bayonet coupling (15) to the elongated central body (1).

6. The safety scalpel according to claim 1, wherein the prismatic guide is formed by two C-shaped elements (18) having a wing (19) that is reduced to form the slot (12).

* * * * *